United States Patent [19]

Barton et al.

[11] 4,136,701

[45] Jan. 30, 1979

[54] RETRACTABLE STIMULATION ELECTRODE APPARATUS

[76] Inventors: Steven A. Barton, 401 S. Brazosport Blvd., Freeport, Tex. 77541; Steven G. Anderson, 107 Poinciana Dr., Lake Jackson, Tex. 77566

[21] Appl. No.: 858,954

[22] Filed: Dec. 9, 1977

[51] Int. Cl.² .............................................. A61N 1/04
[52] U.S. Cl. ................................. 128/418; 128/419 P
[58] Field of Search ..................... 128/404, 418, 419 P

[56] References Cited

U.S. PATENT DOCUMENTS

| | | | |
|---|---|---|---|
| 3,478,234 | 10/1969 | Tachick | 128/418 |
| 3,754,555 | 8/1973 | Schmitt | 128/418 |

FOREIGN PATENT DOCUMENTS

| | | | |
|---|---|---|---|
| 2533766 | 3/1977 | Fed. Rep. of Germany | 128/418 |
| 2539553 | 10/1977 | Fed. Rep. of Germany | 128/418 |

*Primary Examiner*—William E. Kamm
*Attorney, Agent, or Firm*—Jones, Thomas & Askew

[57] ABSTRACT

Electrode apparatus which is used with stimulation devices such as cardiac pacemakers or the like, and which has tissue-engaging members that are selectively retractable from tissue engagement without tearing or otherwise damaging the tissue. One or more tissue-engaging members is retractably mounted within the electrode body. Retraction or extension of the tissue-engaging member is accomplished with an elongated tool which is extendable through the hollow coil that attaches to the body of the electrode apparatus. In one embodiment of the electrode apparatus, the tissue-engaging members are non-rotatably extended and retracted from the apparatus, thereby further minimizing the possibility of damage to body tissue.

13 Claims, 5 Drawing Figures

U.S. Patent        Jan. 30, 1979        4,136,701
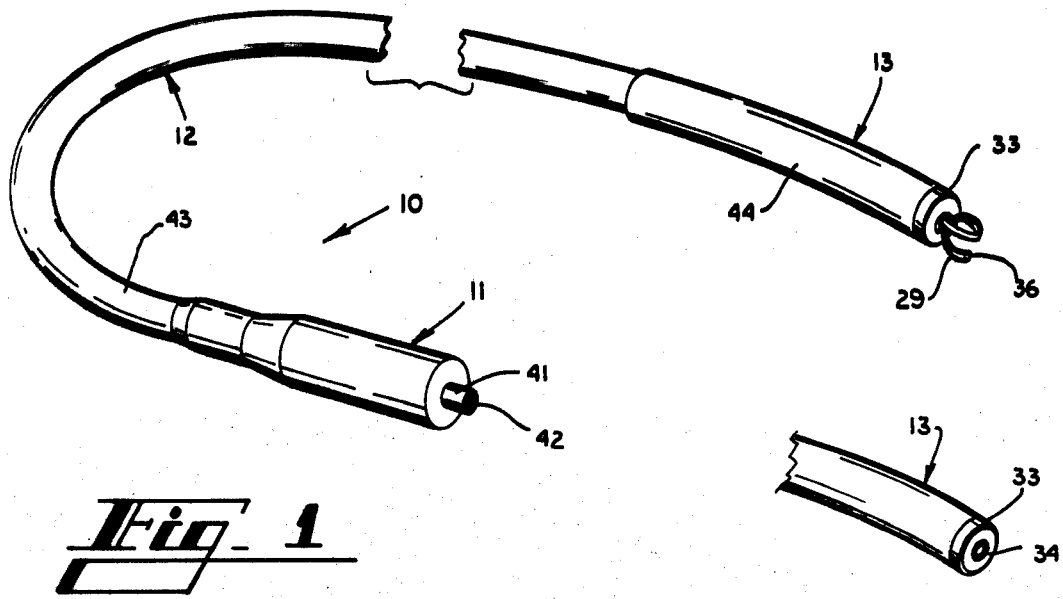
Fig. 1
Fig. 2
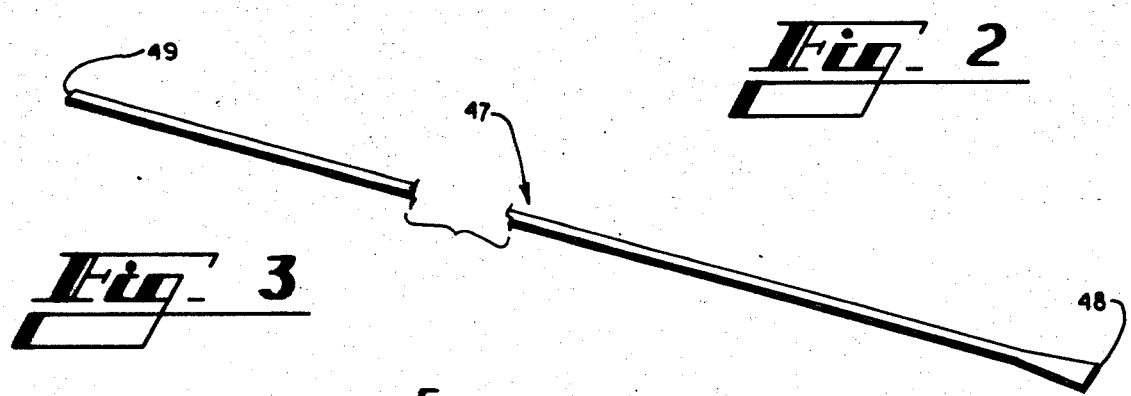
Fig. 3
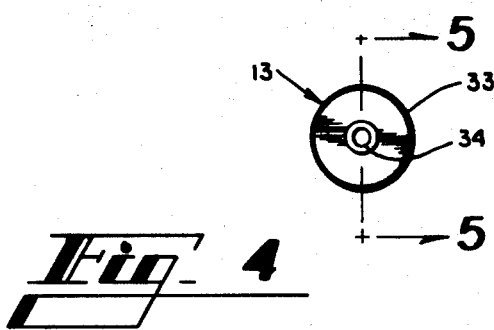
Fig. 4
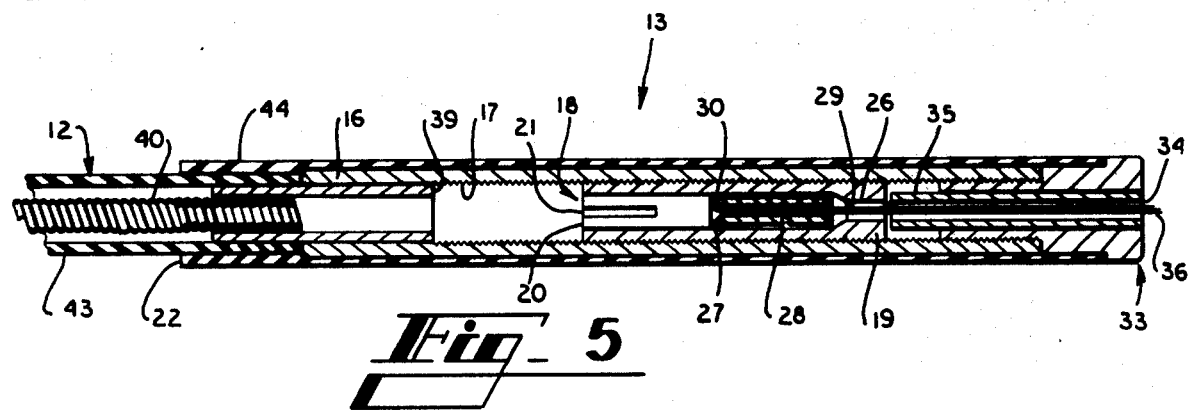
Fig. 5

RETRACTABLE STIMULATION ELECTRODE APPARATUS

This invention relates in general to body tissue stimulation apparatus and in particular to electrode apparatus intended for use with tissue stimulating devices such as cardiac pacemakers or the like.

Pacemakers and other tissue stimulation devices generally operate to provide an electrical signal which is applied to certain body tissue so as to stimulate or otherwise affect the operation of an organ of the body. The actual stimulation signals are typically generated by a pacemaker or other apparatus which may be surgically implanted within the body, but not in direct contact with the heart or other organ to be regulated, and suitable electrical leads must then be provided to supply the signals from the electronic device to the particular organ of the body.

A critical portion of such body electrodes is the element which actually contacts or engages the body tissue to make electrical signal-transfer contact therewith. Some body tissue leads used for pacemaking purposes rely on an electrode having an enlarged tissue-containing tip having a blunt or spherical configuration, devoid of any projections or other sharp edges which might cause damage to body tissue. Such electrodes must be firmly positioned against the appropriate location on a body organ, e.g., the heart, and must in some manner be maintained in the desired position, since there is no mechanical engagment of the blunt electrode end with the body tissue. As a consequence, there is a risk that such body-implantable leads of the prior art can become dislocated so as to move out of signal-transfer contact with the desired area of body tissue, such as by active movement of the body or the like.

Another type of prior-art electrical lead includes relatively pointed electrode members which can project into the surface of the desired body tissue, thereby providing a degree of physical engagement between the electrode and the body. It has been found that such pointed electrodes may cause unwanted and unnecessary tissue damage, however, especially when it becomes necessary for a surgeon to reposition the electrode within the body, since such electrodes as used in cardiac pacemaker applications are frequently inserted through a patient's vein with a catheter. Venous repositioning of prior-art electrodes having tissue-engaging pointed members may be sufficiently damaging that it becomes necessary to surgically remove or reposition the electrode by opening up the chest cavity of the patient. The time, trauma, and expense of such a procedure is self-evident.

Accordingly, it is an object of the present invention to provide an improved electrode apparatus for tissue stimulation.

It is another object of the present invention to provide stimulation electrode apparatus having tissue-engaging means which can be repositioned without causing tissue damage.

It is yet another object of the present invention to provide body implantable electrode apparatus having tissue-engaging means that is selectably retractable into or extendable from the electrode assembly.

Stated in general terms, the electrode apparatus of the present invention comprises a body portion which is connected to a pacemaker or other utilization device by an electrical lead having a hollow passageway along its length, so as to accommodate a manipulating tool. Within the body portion of the electrode apparatus is a movable member which is engageable by the tool when extended through the lead. The movable member within the body of the electrode is connected with one or more tissue-engaging members which are extendable out of the body or retractable into the body when in response to manipulation of the movable member by the tool extended through the passage of the lead. Stated somewhat more specifically, the movable member engages threads within the body to reciprocate within the body is response to being rotated by a tool extended through the lead. It is this reciprocation of the body member which selectably extends or retracts the tissue-engaging means relative to the body. In a particular preferred version of the present invention, a rotating connection is provided between the rotatable member of the electrode body and the tissue-engaging means, so that the tissue-engaging means need not rotate as such means are being extended or retracted relative to the electrode body.

The nature of the present invention as well as other objects and advantages thereof will be more readily apparent from the following discussion of the disclosed embodiment thereof, as shown in the drawings in which:

FIG. 1 is a broken pictorial view showing the disclosed embodiment of the present invention, with tissue-engaging members depicted in extended position;

FIG. 2 is a fragmentary pictorial view of the embodiment shown in FIG. 1, with the tissue-engaging members retracted into the electrode body;

FIG. 3 is a broken pictorial view showing an embodiment of tool which is used for manipulating the disclosed embodiment of the present invention;

FIG. 4 is an end elevation view showing the electrode body of the disclosed embodiment; and FIG. 5 is a section view of the electrode body taken along line 5—5 of FIG. 4.

Turning to the drawings, there is shown generally at 10 an embodiment of electrode apparatus according to the teachings of the present invention. The electrode apparatus 10 includes a connector member 11 designed for attachment to a signal device such as a cardiac pacemaker or the like, a lead portion 12, and an electrode body 13 which is intended to be positioned in proximate relation to the organ to be stimulated. It will be understood by those skilled in the art that all exposed surfaces of the electrode apparatus 10 are constructed of materials such as stainless steel, silicone rubber, or other materials which do not react with the body and which are not damaged by exposure to body fluids.

Details of the electrode body 13 are best seen in FIGS. 4 and 5. The electrode body includes an elongated hollow barrel 16 which is threaded as at 17 along at least a portion of its open interior. Received within the hollow barrel 16 is the movable slug assembly 18, which includes the hollow tube 19 and the closure 20 which is press-fit or otherwise secured into the open end of the hollow tube facing toward the lead-connecting end 22 of the electrode body lead. The exterior of the hollow tube 19 has threads which mate with the threads 17 on the interior of the barrel 16, and the closure 20 is provided with suitable tool-engaging structure such as the open slot 21 which faces toward the lead-connecting end 22 of the electrode body 13. The interior diameter of the hollow tube 19 is reduced toward the tip-confronting end of the tube to provide a relatively narrow aperture 26, so that a chamber 27 is defined within the hollow tube between the aforementioned aperture and the inwardly facing end of the closure 20. Loosely received within the chamber 27 is a hollow tube 28, and the ends 30 of a number of electrodes 29 are secured to the tube 28 within its interior by means of brazing or by any other suitable securement technique. The tube 28 should be received within the chamber 27 with enough play so that the tube can remain in nonrotating relation to the hollow tube 19, when the latter is rotated. It may be desirable to coat the exterior of the tube 28 with a small amount of oil or another suitable lubricant during assembly of the electrode body 13, so as to facilitate the rotation of the hollow tube 19 relative to the tube 28.

The electrodes 29 extend freely through the aperture 26 in the forward end of the hollow tube 19, and extend outwardly through the opening 34 in the hollow tip 33 of the electrode body. The tip 33 has a hollow tube 35 secured within, in coaxial alignment with the aperture 26 in the hollow tube 19, so that the tube 35 provides lateral support and guidance for the electrodes 29. The outer ends 36 comprise the tissue-engaging portion of the present electrode apparatus, and may have any appropriate configuration known to those skilled in the art.

A hollow tube 39 is secured within the interior of the barrel 16 at the lead-connecting end 22 thereof, and a hollow, flexible, electrically-conductive coil 40 is firmly secured within the hollow tube 39. The coil 40, which is preferably made of a material such as stainless steel, Elgilogy (a trademark of Elgin Watch Company), or the like, extends along the length of the lead 12 and is attached to the hollow connector pin 41 (FIG. 1) of the connector member 11. It will be understood that the opening 42 into the hollow connector pin 41 is coaxially aligned with the hollow interior or lumen of the coil 40.

The coil 40 is received within a sheath 43 of a suitable fluid-impervious flexible and electrically-insulating material such as silicon rubber or the like, which is bonded to a sleeve 44 of like or similar material which encloses the barrel 16 and other components of the electrode body 13. It will be understood that the exterior of the connector member 11 is also fabricated from a similar material which is bonded or otherwise secured to the sheath 43 of the lead 12.

The operation of the disclosed embodiment will now be considered. It will be seen that the outer ends 36 of the electrodes 29 may be extended outwardly from the tip 33 to be in tissue-engaging position as shown in FIG. 1, or may be withdrawn within the opening 34 of the electrode body tip as shown in FIG. 2, depending on the longitudinal position of the slug assembly 18 within the barrel 16 of the electrode body. It is assumed that the slug 18 will be rotated within the barrel 16 so as to move toward the end 22 of the electrode body and thereby to withdraw the outer ends 36 of the electrodes, before the electrode apparatus 10 is initially inserted into a patient's body by venous passage or otherwise. Once the surgeon decides that the tip 33 of the electrode body is appropriately positioned adjacent the heart or some other organ of the body, an appropriate tool such as the screwdriver stylet 47 (FIG. 3) is inserted through the opening 42 in the pin 41 so as to extend through the hollow coil 40 and into the hollow interior of the electrode body barrel 16. The stylet 47, which is sufficiently flexible to follow the contour of the lead 12, has a forward end 48 forming a screwdriver tip which is receivable within the slot 21 formed in the closure 20. The tube 39 guides the forward end 48 of the stylet toward the slot 21, in addition to defining a motion stop for the slug 18. The stylet 47 is sufficiently long to permit the back end 49 thereof to extend out of the opening 42 in the pin 41. The stylet may now be rotated so as to rotate the slug 18, thereby longitudinally moving the slug toward the tip 33 of the electrode body 13.

Forward movement of the slug 18 moves the tube 28 forwardly, causing the outer ends 36 of the electrodes 29 to extend outwardly from the tip 33 so as to engage adjacent tissue of the body. The tip 33 of the electrode body 13 is thus more positively supported or maintained in electrical contact with adjacent body tissue. Installation of the electrode apparatus is completed by withdrawing the stylet 47, so that the connector member 11 can be attached to a pacemaker or other suitable electronic apparatus.

If it is desired to reposition the electrode apparatus within the body, or to entirely withdraw the electrode apparatus from the body, the stylet 47 is again extended through the lead 12 to operatively engage the slug 18. The slug is then rotated in the proper direction by the stylet to withdraw the outer ends 36 of the electrodes within the tip 33. The aforementioned non-rotating relation between the tube 28 and the slug 18 allows the electrodes to be extended and withdrawn without rotation, thereby minimizing tissue damage which would otherwise occur if the electrode tips 36 were rotated while engaged with body tissue. Similarly, the tissue-engaging electrode tips 36 may be non-rotatably extended after the electrode body 13 has been repositioned within the patient's body.

It should be understood that the number and style of the electrodes 29 that are herein depicted is by way of example only, and is not considered to be a typical or otherwise limiting factor in the construction and application of retractable electrode apparatus according to the teachings of the present invention. Furthermore, it may be described to provide an electrode with a tissue-engaging member having generally the form or function of a spiral or auger for tissue engagment, in which case it may be desired that the electrode tip should be rotatable to enhance tissue penetration or withdrawl of the electrodes. In that case, it would be appropriate to eliminate the above-described non-rotating relation between the tube 28 and the hollow tube 19.

It will be apparent that the foregoing relates only to a disclosed embodiment of the present invention, and that numerous alterations and modifications may be made therein without departing from the spirit and the scope of the following claims.

What is claimed is:

1. Retractable tissue engaging electrode apparatus, comprising:
   an electrically conductive signal lead means;
   electrode body means connected to said signal lead means and having a conductive portion intended for signal transfer contact with body tissue;
   tissue engaging means associated with said electrode body means and operative to engage body tissue so as to maintain said conductive portion in predetermined signal transfer contact;
   rotatable means within said electrode body means; and
   means operatively associated with said rotatable means to non-rotatably extend or withdraw said tissue engaging means in response to rotation of said rotating means.

2. Apparatus as in claim 1, wherein:

said electrode body means comprises an outer member, and said rotatable means comprises an inner member rotatably received within said outer member;

said inner member having means which is engagable by an actuating member; and said signal lead means includes means operative to guide an actuating member into operative relation with said electrode body means; and said tissue engaging means being operatively associated with said inner member so as to be extended in tissue engaging relation in response to rotation of said inner member in a first direction, and to be withdrawn from said tissue engaging relation in response to rotation in a second direction.

3. Apparatus as in claim 2, wherein said inner member is threadedly engaged with said outer member so that said inner member moves axially along said outer member in response to said rotation, thereby to extend or to retract said tissue engaging means.

4. Apparatus as in claim 2, wherein said signal lead means comprises hollow tubular means defining an internal passage operative to receive and guide said actuating member.

5. Apparatus as in claim 1, further comprising: rotatable means within said termination means; and means operatively associated with said rotating means to nonrotatingly extend or withdraw said tissue engaging means in response to rotation of said rotating means.

6. Retractable tissue engaging electrode apparatus, comprising:

electrode support means having an electrically conductive tissue contacting surface;

at least one tissue engaging member carried by and selectably non-rotatable extendable from and retractable into said electrode support means for engaging body tissue; and rotatable means within said electrode support means and selectably operative to non-rotatably move said tissue engaging member relative to said electrode support means so that said tissue engaging member is selectively extended or retracted from engagement with the tissue which is in proximate location to said tissue contacting surface of said electrode support means.

7. Apparatus as in claim 6, further comprising:

an elongated hollow member extending from said electrode support means and terminating at a location which is remote to said electrode support means, said hollow member being operative to accommodate a tool which extends within said hollow member and is manipulable from said remote location;

said rotatable means within said electrode support means is operative to be engaged for rotation by said tool extending through said hollow member; and means operative in response to rotation of said rotatable means by said tool to move said tissue engaging member to or from said tissue engaging relation.

8. Apparatus as in claim 7, in which:

said hollow member is electrically conductive and is in signal transfer relation with said electrode support means.

9. Apparatus as in claim 6, wherein:

said electrode support means includes a threaded interior portion;

said rotatable means disposed within said electrode support member includes a threaded portion which engages said threaded interior portion;

said rotatable means being rotatable within said electrode support means by manipulation of a tool which is selectably operatively engagable with said electrode support means, so that said rotatable means can be reciprocated within said electrode support member in response to said rotation; and means operatively coupling said tissue engaging member to said rotatable means so that said tissue engaging member is withdrawn into said electrode support means, or is extended therefrom to be in tissue engaging position, in response to rotation of said rotatable means by said tool.

10. Apparatus as in claim 9, wherein said means operatively coupling said tissue engaging means to said rotatable means is inoperative to couple rotation of said rotatable means, so that said tissue engaging means is nonrotatably reciprocated into and out of tissue engaging position.

11. Retractable tissue engaging electrode apparatus comprising:

electrode support means having an electrically conductive tissue contacting surface;

at least one tissue engaging member carried by and selectively non-rotatably extendable and retractable relative to said electrode support means;

rotatable means disposed within said electrode support means for rotation in either of two directions in response to manipulation by a tool insertable into the electrode support means; and means non-rotatably connecting said tissue engaging member and said rotatable means and operative to extend and to retract said tissue engaging member in response to selected rotation of said rotatable means.

12. Apparatus as in claim 11, wherein said rotatable means in operative for rotation by a tool which is removably insertable into said electrode support means.

13. Apparatus as in claim 11, further comprising:

an elongated follow member extending from said electrode support means and terminating at a location which is remote from said electrode support means;

said hollow member being operative to receive a said tool which extends therethrough to rotatably engage said rotatable means and which is manipulable from said remote location.

* * * * *